United States Patent [19]

Kurosaki et al.

[11] Patent Number: 4,670,575

[45] Date of Patent: Jun. 2, 1987

[54] PROCESS FOR PURIFICATION OF PHOSPHORIC MONO ESTERS

[75] Inventors: Tomihiro Kurosaki, Osaka; Junya Wakatsuki, Wakayama; Hisakazu Furugaki, Wakayama; Katsutoshi Kojima, Wakayama, all of Japan

[73] Assignee: Kao Corporation, Tokyo, Japan

[21] Appl. No.: 737,490

[22] Filed: May 24, 1985

[30] Foreign Application Priority Data

Jun. 5, 1984 [JP] Japan .............................. 59-115305
Jul. 3, 1984 [JP] Japan .............................. 59-137777
Jul. 4, 1984 [JP] Japan .............................. 59-138829

[51] Int. Cl.$^4$ .............................................. C07F 9/09
[52] U.S. Cl. ..................................... 558/146; 558/110
[58] Field of Search ................................. 558/110, 146

[56] References Cited

U.S. PATENT DOCUMENTS 2,658,909 11/1953 Crandall et al. ..................... 558/146
4,410,466 10/1983 Schimmel et al. .................. 558/146

*Primary Examiner*—Anton H. Sutto
*Attorney, Agent, or Firm*—Oblon, Fisher, Spivak, McClelland & Maier

[57] ABSTRACT

A novel process for producing a phosphoric monoester which comprises reacting per 1 mole of a linear or branched, saturated or non-saturated aliphatic alcohol having from 8 to 36 carbon atoms, from 2 to 10 moles of a polyphosphoric acid at 100 to 116% concetration converted as orthophosphoric acid in (a) one or more solvents selected from the group consisting of linear or branched saturated aliphatic hydrocarbons having from 4 to 8 carbon atoms and saturated cycloaliphatic hydrocarbons having from 5 to 7 carbon atoms, then adding (b) a lower alcohol having from 1 to 4 carbon atoms and water to the reaction mixture, transferring the orthophosphoric acid to the lower alcohol-aqueous phase to separate it from the phosphoric monoester, and concentrating the thus recovered orthophosphoric acid for reuse. The process reaction proceeds smoothly, separation and purification can be carried out readily and very effectively and the recovered phosphoric acid can be re-used.

6 Claims, 1 Drawing Figure

FIGURE

PROCESS FOR PURIFICATION OF PHOSPHORIC MONO ESTERS

BACKGROUND OF THE INVENTION i. Field of the Invention

This invention concerns a novel process for producing phosphoric monoesters. More specifically, it relates to an extremely advantageous production process for phosphoric monoesters that can conduct the reaction smoothly, provide satisfactory separation and purification of the reaction product and effectively reuse the recovered phosphoric.

ii. Description of the Prior Art

Phosphoric esters of organic hydroxy compounds have been utilized in diversified field of applications such as detergents, fiber processing aids, emulsifiers, rust preventing agents, liquid ion exchangers and pharmaceutical medicines.

Heretofore, a process for reacting phosphorus pentaoxide with an organic hydroxy compound has been known as the process for industrially producing phosphoric esters, in which the reaction product comprises an equimolar mixture of a phosphoric monoester (II) and a phosphoric diester (III) (hereinafter, the mixture is referred to as a sesquiphosphate).

(wherein R' represents a residue of an organic hydroxy compound).

However, the phosphoric monoester and phosphoric diester are greatly different from each other with respect to the physical properties. For instance, while alkali metal salts of monoalkyl phosphates of long-chained alkyl alcohols are excellent as detergents since they are water soluble, have satisfactory foaming and cleaning performance, as well as are less toxic and thus less irritative to skin, dialkyl phosphates are scarcely soluble in water and have no substantial foaming performance. Rather, the dialkyl phosphates show foam suppressing property and, accordingly, said sesqui-phosphates containing monoalkyl phosphates cannot be used as highly foaming detergents.

In view of the above, there has been high demand to industrially produce only phosphoric monoesters selectively with safety and ease, and several processes as described below have been reported.

(1) A method of hydrolyzing monophosphorodichloridate obtained by reacting an alcohol and phosphorus oxychloride (refer to Methoden der Organischen Chemie, edited by K. SASSE, Vol. 12/2, p 163-164, and Japanese Patent Laid-Open No. 64226/1975).

(2) A method of previously adding from 0.5 to 3 mol of water per one mol of phosphorus pentaoxide to an alcohol and then reacting phosphorus pentaoxide (refer to Japanese Patent Publication No. 14416/1966).

(3) A method of reacting orthophosphoric acid and phosphorus pentaoxide with an alcohol (refer to Japanese Patent Publication No. 6730/1967).

(4) A method of reacting an alcohol with a condensed phosphate (polyphosphoric acid) (A. K. Nelson, et at, Inorg. Chem. 2. 775 (1963), or F. B. Clarke, et at, J. Amer. Chem. Soc., 88, 4401 (1966) and Japanese Patent Publication No. 26492/1968).

However, these methods have the following drawbacks and are not satisfactory as industrial processes.

The method (1) produces 3 mol of hydrogen chloride for preparing one mol of monoalkyl phosphate, which results in problems for the disposal of hydrogen chloride and in view of the working circumstances, as well as since an alkyl chloride is by-produced due to hydrogen chloride it is difficult to obtain a satisfactory yield of the monoalkyl phosphate.

In the processes (2) and (3), the ratio of the monoalkyl phosphate can be increased by increasing the amount of water or othophosphoric acid, when only the ratio between the monoalkyl phosphate and the dialkyl phosphate is taken into consideration. However, the reaction ratio of phosphorus is reduced to increase the production amount of orthophosphoric acid. Incorporation of orthophosphoric acid to a final product gives an undesired effect depending on the application uses to thereby restrict the field of applications and reducing the commercial value of the product. For example, in a case of using a monosodium salt of a monoalkyl phosphate derived from a long-chained alkyl alcohol in the form of paste like detergent, the presence of orthophosphoric acid in a great amount will lead to the deposition of disodium phosphate, which is undesirable in view of the use.

The process (4) can selectively produce the monoalkyl phosphate. However, since the amount of orthophosphoric acid by-produced in the reaction substanially agrees with the reciprocal of the average condensation degree of a polyphosphoric acid, orthophosphoric acid is inevitably incorporated into the product to resulting in the problems as described above.

Accordingly, these prior processes can not produce monoalkyl phosphates selectively at a high purity, for example, with no incorporation of orthophosphoric acid.

By the way, as a method of removing orthophosphoric acid from the mixture of a phosphoric ester and orthophosphoric acid, only the method of Nelson et al for extracting phosphoric esters to remove orthophosphoric acid by the use of an ethyl ester has been known (Inorg. Chem. 2, 775 (1963)). However, since ethyl ether is a low boiling point solvent having an extremely low flash point and further, peroxide is gradually resulted, it may cause an explosive danger if the peroxide is accumulated and gives undesired effect to the human body, thereby inviting an industrial problem.

The present inventors have made a study on various solvents other than ethyl ether. However, it has been found that use of etheric solvent such as diisopropyl ether is not preferred since it involves the danger of explosion due to the accumulation of peroxide, although the removal of orthophosphoric acid is possible as in the case of ethyl ether. Furthermore, other solvents could not provide a satisfactory result in a single solvent system since the phosphoric ester itself is a strong emulsifier resulting in the formulation of a stable emulsion system as a whole.

SUMMARY OF THE INVENTION

In view of the above, development of an industrial process has been in great demand that can produce a phosphoric monoester selectively and at a high yield from an alcohol and a polyphosphoric acid and that allows isolation of the phosphoric monoester with ease from by-produced orthophosphoric acid.

The present inventors have made a study under such circumstance and have found that in a case where a mixture consisting of a phosphoric ester and orthophosphoric acid is subjected to separation by extraction with a combination of (a) a linear or branched saturated hydrocarbon having from 4 to 8 carbon atoms or a saturated cycloaliphatic hydrocarbon having from 5 to 7 carbon atoms and (b) a lower alcohol having from 1 to 4 carbon atoms and water, a phosphoric ester can be isolated into the oily layer of the solvent (a) and orthophosphoric acid can be separated into the aqueous layer of the solvent (b) effectively.

The inventors have further found that the reaction between the alcohol and the polyphosphoric acid advantageously proceeds in the solvent (a), and that orthophosphoric acid can be separated and removed by an extremely simple procedure through extraction by adding the solvent (b) to the reaction mixture to thereby obtain the phosphoric monoester of a high purity and that the thus recovered orthophosphoric acid can be reused through concentration.

Accordingly, the first invention of the present application provides a process for producing a phosphoric monoester which comprises reacting one mol of a linear or branched saturated or non-saturated aliphatic alcohol having from 8 to 36 carbon atoms and from 2 to 10 mol of a polyphosphoric acid at 100-116% concentration converted to the orthophosphoric acid in (a) one or more solvents selected from the group consisting of linear or branched saturated aliphatic hydrocarbons having from 4 to 8 carbon atoms and saturated cycloaliphatic hydrocarbons having from 5 to 7 carbon atoms, then adding (b) a lower alcohol having from 1 to 4 carbon atoms and water to the reaction mixture, transferring orthophosphoric acid to the lower alcohol-aqueous phase to separate it from the phosphoric monoester, and concentrating the thus recovered orthophosphoric acid for re-use.

Further, the second invention of the present application provides a process for purifying a phosphoric ester which comprises adding the solvent (a) and the solvent (b) to a mixture containing a phosphoric ester and orthophosphoric acid, and extracting the phosphoric ester into the hydrocarbon layer.

Furthermore, the third invention of the present application provides a process for purifying a phosphoric ester which comprises adding the solvent (a) and the solvent (b) to a mixture containing the phosphoric ester and orthophosphoric acid, extracting to isolate the phosphoric ester into a hydrocarbon layer, removing a lower alcohol and water incorporated into the hydrocarbon layer through azeotropic distillation and then recrystallizing or topping the residue.

DETAILED DESCRIPTION OF THE INVENTION AND PREFERRED EMBODIMENTS

The aliphatic alcohol for use in the first invention of the present applicaton can include, for example, octyl alchol, dodecyl alcohol, hexadecyl alcohol, octadecyl alchol, oleyl alchol, 2-hexyldecyl alcohol, 2-decylpentadecyl alcohol and 2-hexadecyleicosyl alcohol.

The linear or branched saturated aliphatic hydrocarbon having from 4 to 8 carbon atoms or the saturated cyclo-aliphatic hydrocarbon having from 5 to 7 carbon atoms for use as the solvent (a) in this invention can include, for example, butane, n-pentane, n-hexane, n-heptane and cyclohexane, with n-heptane, n-hexane and cyclohexane being preferred and, further, n-hexane being particularly preferred. The lower alcohol for use as the solvent (b) in this invention can include methanol, ethanol, n-propanol, isopropanol and n-butanol, with ethanol and isopropanol being preferred and, further, isopropanol being particularly preferred.

While the molar ratio between the polyphosphoric acid and the alcohol in the reaction of the first invention according to the present application can be selected optionally, the present inventors have found an optimum condition under which the alcohol can be reacted sufficiently (to more than 98% conversion rate), that is, a relationship between the concentration of a polyphosphoric acid and the reaction molar ratio r (r=[number of mols of phosphoric acid converted as orthophosphoric acid]/[number of mols of alcohol], r represents such a molar ratio hereinafter) which reduces the unreacted alcohol to as little as possible and also minimizes excess phosphoric acid remaining upon completion of the reaction. The relationship is as shown in Table 1.

TABLE 1

| Concentration of polyphosphoric acid used (converted as orthophosphoric acid wt %) | Optimum reaction molar ratio r |
|---|---|
| 100 | 10 |
| 105 | 5 |
| 112 | 5 |
| 112 | 3 |
| 116 | 2 |

Further, if the amount of the solvent (a) added as the reaction medium is insufficient, a highly viscous gel-like reaction mixture results yielding a difficulty in uniform stirring. Accordingly, the amount of the solvent is usually from 0.5 to 3 parts by weight and, particularly, from 1 to 2 parts by weight per one part by weight of the alcohol used in the reaction.

Further, although the reaction temperature is not a determinative factor in this reaction, higher temperatures are desired since they can shorten the reaction time. Thus the reaction is preferably carried out near the boiling point of the solvent (a) used as the reaction medium. However, a temperature in excess of 100° C. is not preferred since the phosphoric ester itself is thermally decomposed. Further, the reaction may be carried out optionally in a pressurized system.

Upon practicing this invention, if a polyphosphoric acid or pyrophosphoric ester is present at the completion of the reaction, water may desirably be added for hydrolysis. Since the presence of a pyrophosphoric ester worsens the separatability in the subsequent step of extracting to separate orthophosphoric acid, and the extraction therefore takes more time, conduction of the hydrolyzing step is highly desired. In this case, it is sufficient to add such an amount of water to hydrolyze the pyrophosphoric acid present such that the concentration of the orthophosphoric acid is preferably from 85 to 90% when considering only orthophosphoric acid and water in the composition after the hydrolysis. The temperature and time required for the hydrolysis are dependent on the concentration of polyphosphoric acid, that is, from 2 to 3 hours at 80° C. for the 105% concentration of polyphosphoric acid and from 4 to 5 hours at 80° C. for 112% concentration of the polyphosphoric acid.

When orthophosphoric acid is extracted to separate it from the reaction mixture thus obtained, a lower alcohol having from 1 to 4 carbon atoms and water (solvent (b)) and, optionally, the solvent (a) are added such that the extrudate comprises the composition as described below. Desirably, the solvent (b) is added such that water is contained by from 0.5 to 3 parts by weight, preferably, from 0.7 to 2 parts by weight and the lower alcohol is contained by from 0.1 to 15 parts by weight, preferably, from 0.1 to 10 parts by weight based on one part by weight of the alcohol used in the reaction. Further, the solvent (a) is desirably added such that it is contained by from 0.5 to 10 parts by weight, preferably, from 1 to 3 parts by weight including the amount used in the reaction.

When the liquid mixture containing the phosphoric ester and orthophosphoric acid is mixed by means of agitation or the like and then stood still, the mixture separates in a short time into an oily layer (lighter liquid layer) with a high content of the phosphoric ester and an aqueous layer (heavier liquid layer) with a high content of orthophosphoric acid. The extraction procedure may be carried out optionally under heating. In a case where the removal of orthophosphoric acid is still insufficient in this extracting procedure, the oily layer after being separated from the aqueous layer with a high orthophosphoric acid content may further be subjected to the same extracting procedure while adding water and the lower alcohol each in the same amounts as above. The extracting procedure may be carried out either batchwise or continuously.

The aqueous layer with a high content of orthophosphoric acid thus obtained (hereinafter referred to as a recovered phosphoric acid) contains the lower alcohol and a small amount of the phosphoric ester in addition to orthophosphoric acid and water. By the way, when water is distilled off from an aqueous solution of orthophosphoric acid under an ambient or reduced pressure, a condensed phosphate (polyphosphoric acid) can be obtained. (Phosphorus and its Compounds, edited by VAN WAZER, vol. I, p 773 or B. J. Fontana, J. Amer. Chem. Soc., 73, 3348, (1951), etc). However, a high temperature more than 100° C. under a reduced pressure of 2 mmHg is required in order to obtain phosphoric acid at a concentration of higher than 100% converted as orthophosphoric acid. If the material of the processing apparatus is made of metals, corrosion or the material for the apparatus due to phosphoric acid will result in significant problems in the industrial processes in view of the durability of the apparatus and the incorporation of leached metals into the final product at such a high temperature condition. Fortunately, it has been known tha Hastelloy type nickel alloys have an excellent corrosion resistance at a temperature near 150° C. as the stainless type heat and corrosion resistant alloy materials (Saji, et al, Metal surface Technology, 13, 19, (1962) or R. K. Swandby, Chemical Engineering, November 12, 186 (1962) etc). Further, there can be found excellent carbon type materials in addition to metal materials.

Accordingly, it is possible to industrially obtain a condensed phosphate (polyphosphoric acid) at a concentration from 100 to 110% converted as orthophosphoric acid. Further, the lower alcohol and a small amount of the phosphoric ester contained in the aqueous layer with a high content of orthophosphoric acid gives no hindrance to the concentrating procedure in this invention.

The concentration step may be carried out either continuously or batchwise.

While any concentration between 100 and 116% may be used for the polyphosphoric acid converted as orthophosphoric acid in this invention, a polyphosphoric acid at 100 to 110% concentration can be obtained industrially with ease as described above. By the way, in the case of re-using the recovered orthophosphoric acid through concentration, the amount of phosphoric acid consumed in the reaction has to be compensated. Assuming that one mol of alcohol and r mol (r=reaction molar ration, r=2 to 10) of a polyphosphoric acid are reacted in the phosphorylation, since substantially 100% of the alcohol is converted into a phosphoric monoester, (r−1) mols of unreacted orthophosphoric acid result. In an attempt to supplement the one mole of phosphoric acid consumed in the reaction by phosphorus pentaoxide ($P_2O_5$, corresponding to a 138% condensed phosphate converted as orthophosphoric acid), a degree of concentration (%) required for the recovered (r−1) mols of phosphoric acid in order to attain the same concentration of phosphoric acid as that in the reaction can be calculated. For instance, in the case of using a polyphosphoric acid at 116% concentration (reaction molar ratio r=2), if (r−1)=(2−1)=1 mol of phosphoric acid is concentrated to 100% (98 g), and one mol of phosphoric acid consumed in the reaction is supplemented with phosphorus pentaoxide (138% polyphosphoric acid, 71 g), 2 mols of 116% phosphoric acid (169 g) can be obtained, which are usable in the subsequent reaction. In another case, where a 112% phosphoric acid is used (reaction molar ratio r=3), if the recovered (r−1)=(3−1)=2 mols of phosphoric acid are concentrated to 102% (192 g) and one mol of phosphoric acid consumed in the reaction is supplemented by the phosphorus pentaoxide (71 g), 3 moles of 112% polyphosphoric acid (263 g) can be obtained. Accordingly, in the case of supplementing the consumed phosphoric acid with phosphorus pentaoxide, it is sufficient to obtain a polyphosphoric acid up to 105% converted as orthophosphoric acid.

However, since arsenic is inevitably incorporated in phosphorus pentaoxide in view of the production step, this has to be taken into consideration in a case where the obtained phosphoric monoester is used in such an application where it is in direct contact with skin. Accordingly, in cases where the phosphoric monoester is used as cosmetic materials, detergents, pharmaceutical medicines or the like, it is desirable in this invention to employ 75% or 85% orthophosphoric acid containing substantially no arsenic, which is prepared through the procedure of utilizing hydrogen sulfide in the production step to precipitate and filter out arsenic as arsenic sulfide. The phosphoric acid is concentrated to 100-110% converted as orthophosphoric acid in the concentration step, which is reacted at the reaction molar ratio r=4-10, after which the phosphoric acid content consumed in the reaction may be supplemented with orthophosphoric acid of the same quality as above.

However, referring to arsenic and also to heavy metals leached out from a concentrating apparatus, since they are distributed at a ratio inherent to the metal into the orthophosphoric acid layer in the step of extracting to separate orthophosphoric acid, and gradually accumulated in the phosphoric acid which is being recovered and re-used, the amount of metals incorporated into the final product can be removed. Further, it has been known that arsenic in orthophosphoric acid can be removed as arsenic sulfide through precipitation and filtration by utilizing hydrogen sulfide as described above, as well as that the heavy metals in orthophosphoric acid can be purified through solvent extraction (Japanese Patent Laid-Open No. 63692/1974). As described above, the recovered orthophosphoric acid in this invention can be recyclically used through dehydrating concentration and, if required, concentration by the addition of phosphorus pentaoxide, which is important from an economical point of view.

Since the oily layer with a high phosphoric monoester content obtained by effectively separating to remove orthophosphoric acid according to this invention contains the lower alcohol and water in additon to the phosphoric ester and the solvent (a), the desired phosphoric monoester can be obtained by merely distilling off the solvent (a), the lower alcohol and water, or by azeotropically removing the lower alcohol and water by the further addition of the solvent (a) depending on the application.

While the purification process of the second invention of the present application may be applied to any phosphoric ester, it is particularly effective when used for the purification of a phosphoric ester comprising the phosphoric monoester represented by the following general formula (I) as the main ingredient.

(I)

(where in R represents a linear or branched alkyl or alkenyl group having from 8 to 36 carbon atoms.

Since the compound represented by the general formula (I) has an intense emulsifying effect, no satisfactory result can be obtained by any other process than that of this invention.

The compound represented by the general formula (I) can include, for example, monoctyl phosphate, monodecyl phosphate, monooctadecyl phosphate, monotetracosyl phosphate, monooctacosyl phosphate, monooctenyl phosphate, monooctadecenyl phosphate, monotetracosenyl phosphate, mono-2-hexyldecyl phosphate, mono-2-octylundecyl phosphate and mono-2-tetradecyloctadecyl phosphate.

The amount of the solvent (a) used in this purification process is properly determined depending on the kind of phosphoric esters or the like and it is usually from 0.5 to 10 parts by weight based on one part by weight of the phosphoric ester. Further, the ratio of the lower alcohol to water as the solvent (b) is properly determined depending on the kind of the lower alcohols and the like, and the lower alcohol is used usually from 0.1 to 5 parts by weight and, preferably, from 0.3 to 1 part by weight based on one part by weight of water. The total amount of the solvent (b) used in this process is properly determined depending on the above-mentioned ratio or the like and it is usually from 0.5 to 80 parts by weight based on one part by weight of orthophosphoric acid.

When the solvents (a) and (b) according to this invention are used, the phosphoric ester is separated into the oily layer (lighter liquid layer) as the solvent (a) while the orthophosphoric acid can be separated into the aqueous layer (heavier liquid layer) as the solvent (b) effectively.

More specifically, the purification process according to this invention is carried out by adding and stirring from 0.5 to 10 parts by weight, preferably, from 1 to 3 parts by weight of an aliphatic hydrocarbon or cyloaliphatic hydrocarbon and from 0.1 to 5 parts by weight, preferably, from 0.3 to 1 part by weight of a lower alcohol to one part by weight of water to a mixture of a phosphoric ester and orthophosphoric acid, then allowing the mixture to stand still for a while and separating into an oily layer and an aqueous layer. If required, the above-mentioned procedures may be repeated after the separation and removal of the aqueous layer by a further addition of an aqueous solution of a lower alcohol.

The procedures may be carried out either under an ambient temperature or under warming.

The purification process according to this invention may be carried out either batchwise or continuously.

The purified phosphoric ester (solution) obtained by the purification process according to this invention may be used as it is or after further being purified in a conventional manner.

The third invention of the present application is carried out by heating, to a temperature above the boiling point of the solvent, the oily layer (hydrocarbon layer) with a high phosphoric ester content obtained in the second invention either as it is or after further adding thereto batchwise or continuously the same solvent as the saturated aliphatic hydrocarbon or saturated cycloaliphatic hydrocarbon used in extracting separation in an amount of from 10 to 30 parts by weight, preferably, from 10 to 15 parts by weight based on water used upon extraction, azeotropically distilling off the water and the lower alcohol thereby removing the water and the lower alcohol in the aqueous layer, then removing the remaining saturated aliphatic hydrocarbon or cycloaliphatic hydrocarbon from the thus obtained residue through topping.

The purification process according to the third invention is further required in addition to the purification process of the second invention for the reason described below.

If the hydrocarbon layer separated through extraction by the process according to the second invention is directly subjected to recrystallization or topping, the incorporated water and lower alcohol provide problems. For instance, in the case of recrystallization, if water is present in the oily layer, the crystallinity is reduced thereby requiring a lower temperature for the crystallization. In a case where the lower alcohol is present, the solubility of the phosphoric ester to the saturated aliphatic hydrocarbon or saturated cycloaliphatic hydrocarbon employed is increased to reduce the recovery rate due to crystallization of the phosphoric ester.

Referring to the case of the topping, where the solvent ingredients are distilled off under a reduced pressure from the phosphoric ester layer, although the saturated aliphatic hydrocarbon or saturated cycloaliphatic hydrocarbon can be distilled off with ease, distillation of the water and the lower alcohol in the phosphoric ester is relatively difficult. Distillation under warming condition would also be difficult since the aimed phosphoric ester itself decomposes at 100° C.

The foregoing drawbacks can be overcome by the process according to the third invention.

A phosphoric ester containing no substantial orthophosphoric acid can be obtained by the processes as described above. In the case of a crystalline phosphoric ester, a phosphoric ester at a higher purity can be obtained by adding the same or different solvent (a) as used upon extracting separation of the above-mentioned residue in a predetermined amount, preferably, from 1 to 20 parts by weight based on one part by weight of the phosphoric ester and then cooling the mixture to deposit the crystals of the phosphoric ester through recrystallization.

This invention will now be described referring to examples.

EXAMPLE 1

From 75% orthophosphoric acid at the grade of food additives (for example, 75% phosphoric acid for use in food additives made by Nihon Kagaku Kogyo K.K.: quality standard; heavy metal (as Pb) less than 0.0001%, iron (Fe) less than 0.0001 and arsenic (As) 0.0001%), a polyphosphoric acid at 105% concentration converted as orthophosphoric acid was obtained under the conditions of a reduced pressure at 2 mmHg and a temperature of from 150° to 160° C. by using a vessel made of Hastelloy metals.

243 g (1.3 mol) of dodecyl alcohol (hydroxy value 300) and 243 g of n-hexane were supplied and mixed sufficiently in a pressure-proof reaction vessel. 607 g of the polyphosphoric acid at 105% concentration (6.5 mol converted as orthophosphoric acid) obtained as described above were sufficiently stirred to the liquid mixture, which was added dropwise while being kept at 70° C. After the completion of the dropping, the stirring was continued for further 10 hours while maintaining the temperature at 80° C. The pressure inside the reaction vessel was 0.8 kg/cm$^2$G. After the reaction was over, 60.5 g of water were added and the stirring was continued for 3 hours while maintaining the temperature at 80° C. to carry out hydrolysis. As the result of analysis at this stage 1.25 mol (334 g) of monododecyl phosphate and 0.016 mol (6.76 g) of didocecyl phosphate were produced and 5.24 mol (513.5 g) of orthophosphoric acid (alcohol conversion rate 98.6%) were contained.

In this analysis, the sample was extracted with ethyl ether and an aqueous 0.1N hydrochloric acid solution to isolate and separate the phosphoric ester into the ethyl ether layer and orthophosphoric acid into the aqueous 0.1N hydrochloric acid layer. Then, they were respectively titrated with an alkali, for example, potassium hydroxide by using an automatic potentiometric titrator to determine the content of monoalkyl phosphate, dialkyl phosphate and orthophosphoric acid. More specifically, in the ethyl ether layer, the sample, was subjected, after topping the ethyl ether, to the potentiometric titration in an aqueous ethanol solution with potassium hydroxide, to determine the content of the monoalkyl phosphate and the dialkyl phosphate based on the first equivalent point and the second equivalent point.

Further, the aqueous 0.1N hydrochloric acid solution was subjected as it was to the potentiometric titration with potassium hydroxide to determine the content of the orthophosphoric acid due to the difference between the first and second equivalent points (the same analytical method was used also in the subsequent examples and comparative examples, the analytical method is hereinafter referred to as an ethyl ether extraction method).

Furthermore, by extracting the sample with petroleum ether after the sample had been dissolved in ethanol and neutralized with an aqueous solution of triethanol amine, the non-ionic ingredient, that is, the dodecyl alcohol in the sample was extracted into the petroleum ether layer and the content of the unreacted alcohol can be determined by subsequently distilling off the petroleum ether (refer to Japanese Patent Laid-Open No. 87856/1981. The analytical method is hereinafter referred to as a petroleum ether extraction method). The amount of the unreacted dodecyl alcohol determined by this process was 3.7 g (0.02 mol) and the alcohol conversion rate was 98.5%, which well agreed with the analytical data obtained by the previous ethyl ether extraction method.

The hydrolyzate was cooled at 50° C. and transferred into an extraction vessel, to which 243 g of n-hexane, 89.7 g of isopropanol and 189 g of water were added and mixed under sufficient stirring. After 30 minutes mixing, the stirring was interrupted and the mixture was left still while maintaining the temperature at 50° C., whereby the mixture was rapidly separated into the n-hexane layer (upper layer) and the aqueous layer (lower layer). After separating to remove the lower layer (hereinafter referred to as the lower layer (1), 712.5 g), 138 g of isopropanol and 363 g of water were further added to the remaining upper layer, which was subjected to the same procedures as above and separated again in to the n-hexane layer and the aqueous layer, the latter being separated to remove (hereinafter referred to the lower layer (2), 397.5 g). The thus obtained n-hexane layer (1066 g) contained 1.24 mol (331 g) of monododecyl phosphate, 0.015 mol (6.7 g) of didodecyl phosphate and 0.10 mol (9.8 g) of orthophosphoric acid (recovery rate for phosphoric ester 99.1%, removal rate for phosphoric acid 98.1%), as the result of the same ethyl ether extraction method as above. While the n-hexane layer contained water and isopropanol, they could be removed by azeotropic distillation while adding n-hexane.

The solution of monododecyl phosphate in n-hexane thus obtained was crystallized by cooling down to 0° to 5° C. to crystallize monododecyl phosphate and after collecting the crystals through filtration, n-hexane was distilled off under a reduced pressure to obtain 337.2 g of white crystals. Upon analyzing the crystals by the ethyl ether extraction method and the petroleum ether extraction method as described above, it was confirmed that they contained 324.7 g of monododecyl phosphate, 2.5 g of didodecyl phosphate, 7.8 g of orthophosphoric acid and 2.2 g of dodecyl alchol. The hue of the product was 6 when represented by klett number (the klett number is a value obtained by measuring the light absorption of a 10% ethanol solution of the specimen, for a 10 mm specimen cell at a 420 nm wavelength by a spectrophotometer using ethanol as a reference and multiplying the thus obtained light absorption value by a coefficient 1000).

Further, the thus recovered 1110 g of phosphoric acid (lower layer (1)+lower layer (2)) contained 5.13 mol (503 g) of orthophosphoric acid and 0.01 mol (2.7 g) of monododecyl phosphate. 183 g (1.4 mol) of 75% phosphoric acid at the foods additive grade were supplemented to the recovered phosphoric acid and concentrated in the same manner as described above to obtain 606 g of 105.1% polyphosphoric acid (6.5 mol converted as orthophosphoric acid). The hue of the polyphosphoric acid showed no change at all, in the hue or the like as compared with that in the phosphoric acid used initially. Further, the polyphosphoric acid was used for the reaction in the same manner as above by dropwise addition into the n-hexane solution (243 g) of 243 g (1.3 mol) of dodecyl alcohol and hydrolysis was carried out. As the result of analysis, 1.275 mol (340.5 g) of monododecyl phosphate, 0.012 mol (5.2 g) of didodecyl phosphate and 5.21 mol (510.6 g) of orthophosphoric acid (99.0% alcohol conversion rate).

The hydrolyzate was cooled and subjected to the same extracting procedures as described above (the amounts of water and isopropanol added, as well as the conditions for the procedures were the same as described above), followed by removal of orthophosphoric acid to obtain 1060 g of a n-hexane layer. It contained 1.26 mol (336 g) of monododecyl phosphate, 0.011 mol (4.8 g) of didodecyl phosphate, and 0.08 mol (7.8 g) of orthophosphoric acid (98.6% recovery rate for phosphoric ester and 98.5% removal rate for orthophosphoric acid).

Water and isopropanol were azeotropically distilled off in the same manner as above from the n-hexane layer, which is cooled, crystallized and filtered and, thereafter, n-hexane was distilled off to obtain 337.9 g of white crystals. As the result of the analysis for the crystals they contained 329.3 g of monododecyl phosphate 1.9 g of didodecyl phosphate, 5.5 g of orthophosphoric acid and 1.2 g of dodecyl alcohol. The hue of the product was 8 as represented by the klett number.

The thus recovered 1115 g of phosphoric acid contained 5.13 mol (503 g) of orthophosphoric acid and 0.017 mol (4.5 g) of monododecyl phosphate. 183 g (1.4 mol) of 75% phosphoric acid at food additive grade were supplemented to the recovered phosphoric acid, which was subjected to the same concentration as described above to obtain 607 g of 105% polyphosphoric acid (6.5 mol converted as orthophosphoric acid).

Further, the thus obtained polyphosphoric acid was used in the same reaction, hydrolysis and extraction as described above. Water and isopropanol were distilled off from the thus obtained n-hexane layer, which was cooled, crystallized and filtered and the n-hexane was distilled off to obtain 335.5 g of white crystals. As the result of the analysis for the crystals, they contained 325.8 g of monododecyl phosphate, 2.0 g of didodecyl phosphate, 6.0 g of orthophosphoric acid and 1.7 g of dodecyl alcohol. The hue of the product was 8 as represented by the klett number.

Each of a series of three final products obtained according to this example contained 1 ppm or less of heavy metals (cosmetic material standards; according to heavy metal test method) and also contained 1 ppm or less of arsenic (atomic absorption analysis).

REFERENCE EXAMPLE 1

With an aim of examining the distribution of heavy metals, the same procedures as in Example 1 were carried out using 105% polyphosphoric acid in which Hastelloy metals used for the concentration apparatus were leached out. 89.6 g (0.48 mol) of dodecyl alcohol and 89.6 g of n-hexane were added into a glass vessel while mixing. Further, 224.1 g of 105% polyphosphoric acid (2.4 mol converted as orthophosphoric acid, containing Ni: 590 ppm (132 mg), Mo: 380 ppm (85.1 mg) and Fe: 46 ppm (10.3 mg)) was added and reacted at 70° C. for 12 hours. After the reaction was over, 22.5 g of water was added and further stirred at 70° C. for three hours to conduct hydrolysis. 89.6 g of n-hexane, 33.0 g of isopropanol and 66.7 g of water were added to the thus obtained mixture at 50° C., mixed under stirring, allowed for stand still and then the aqueous layer was separated to eliminate in the same manner as in Example 1 (lower layer (1), 250.7 g). 49.7 g of isopropanol and 133.7 g of water were further added to the residual n-hexane layer, which was subjected to the same procedures as in Example 1 to separate to eliminate the aqueous layer (lower layer (2), 147.5 g).

The thus recovered 398.2 of phosphoric acid (lower layer (1)+lower layer (2)) contained 360 ppm (143 mg) of Ni, 101 ppm (40.2 mg) of Mo and 13.7 ppm (5.5 mg) of Fe. Further, 400.0 g of the n-hexane layer containing the phosphoric ester (containing 120 g of monododecyl phosphate, 2.6 g of didodecyl phosphate and 4.2 g of orthophosphoric acid) contained 11.3 ppm (4.5 mg) of Ni, 42.0 ppm (16.8 mg) of Mo and 6.0 ppm (2.4 mg) of Fe.

EXAMPLE 2

81.0 g (0.62 mol) of 75% orthophosphoric acid at the foods additive grade were concentrated in the same manner as in Example 1 to obtain 59.2 g of 102.6% polyphosphoric acid converted as orthophosphoric acid. 22.1 g (0.155 mol) of guaranteed reagent grade phosphorus pentaoxide (purity 99.5%, quality standard: 0.003% or less As) were added and sufficiently mixed to the polyphosphoric acid to obtain 81.3 g of 112.1% polyphosphoric acid (0.93 mol converted as orthophosphoric acid).

75.9 g (0.31 mol) of hexadecyl alcohol (hydroxy value 232) and 75.9 g of n-hexane were added to a reaction vessel and while mixing, 81.3 g of 112.1% polyphosphoric acid (0.93 mol) obtained as described above was added thereto. After the addition was over, the stirring was continued at 70° C. for 12 hours. After the reaction was over, 10.5 g of water was added and the stirring was further continued at 70° C. for 6 hours to carry out hydrolysis. When analyzed at this stage by the ethyl ether extraction method in the same manner as in Example 1, 0.301 mol (96.9 g) of monohexadecyl phosphate and 0.003 mol (1.64 g) of dihexadecyl phosphate were formed and 0.627 mol (61.5 g) of orthophosphoric acid were contained (99% conversion rate of alcohol).

The hydrolyzate was cooled to 50° C. and transferred into an extraction vessel, to which 151.7 g of n-hexane, 75.9 g of isopropanol and 75.9 of water were added and mixed under sufficient stirring. After 30 minutes mixing, the stirring was interrupted and when the mixture was allowed to stand still while maintaining the temperature at 50° C., it rapidly separated into a n-hexane layer (upper layer) and an aqueous layer (lower layer). After separating to remove the lower layer (hereinafter referred to as a lower layer (1), 134.0 g), 15.2 g of isopropanol and 75.9 g of water were further added to the residual upper layer, which was separated again into a n-hexane layer and an aqueous layer by the same procedures as described above to separate and remove the aqueous layer (hereinafter referred to as the lower layer (2), 84.8 g). The thus obtained n-hexane layer (419 g) contained, as the result of analysis by the ethyl ether extraction method, 0.298 mol (95.9 g) of monohexadecyl phosphate, 0.003 mol (1.6 g) of dihexadecyl phosphate and 0.011 mol (1.08 g) of orthophosphoric acid (99% recovery rate for phosphoric ester, 98% removal rate for orthophosphoric acid).

Further, the thus recovered 218.8 g of phosphoric acid (lower layer (1)+lower layer (2)) contained 0.61 mol (59.8 g) of orthophosphoric acid, to which 75% orthophosphoric acid at the food additve grade was supplemented as required, and which was concentrated to 102 to 103% concentration converted as orthophosphoric acid in the same manner as described above, then, phosphorus pentaoxide was added in the same quantity ratio as described above and mixed sufficiently to obtain 112% polyphosphoric acid.

As the result of analysis for arsenic with an aim of examining the distribution thereof, arsenic was contained by 7.0 ppm (0.57 mg) in 81.3 g of 112% polyphosphoric acid, by 2.1 ppm (0.46 mg) in 218.8 g of the recovered phosphoric acid and by 0.53 ppm (0.053 mg) in 99.4 g of phosphoric ester (containing 95.9 g of monohexadecyl phosphate) prepared by azeotropically distilling off isopropanol and water contained in the n-hexane layer containing phosphoric ester by further adding n-hexane and, thereafter, distilling off n-hexane.

EXAMPLE 3

121.5 g (0.93 mol) of 75% orthophosphoric acid at the food additive grade was concentrated in the same manner as in Example 1 to obtain 90.7 of 100.5% polyphosphoric acid converted as orthophosphoric acid. 66.4 g (0.465 mol) of phosphorus pentaoxide of the same guaranteed reagent as in Example 2 was added and sufficiently mixed to the polyphosphoric acid to obtain 157.1 g (1.86 mol converted as orthophosphoric acid) of 116% polyphosphoric acid.

330 g (0.93 mol) of 2-decylpentadecyl alcohol (hydroxyl value 158) and 350 g of n-hexane were added to a reaction vessel and, while mixing sufficiently, 157.1 g (1.86 mol) of 116% polyphosphoric acid obtained as described above was added thereto. After the addition was over, the stirring was continued at 70° C. for 8 hours. After the reaction was over, 40 g of water was added and the stirring was further continued at 70° C. for 8 hours to carry out hydrolysis. When analyzed at this stage by the ethyl ether extraction method in the same manner as in Examle 1, 0.849 mol (369.3 g) of mono-2-decylpentadecyl phosphate and 0.036 mol (27.8 g) of di-2-decylpentadecyl phosphate were formed and 0.970 mol (95.1 g) of orthophosphoric acid were contained (99% conversion rate of alcohol).

The hydrolyzate was cooled to 50° C. and transferred into an extraction vessel, to which 350 g of n-hexane, 136 g of ethanol and 330 g of water were added and mixed under sufficient stirring. After 30 minutes mixing, the stirring was interrupted and when the mixture was allowed to stand still while maintaining the temperature at 50° C., it rapidly separated into a n-hexane layer (upper layer) and an aqueuous layer (lower layer). After separating and removing the lower layer (hereinafter referred to as a lower layer (1), 485 g), 140 g of ethanol and 330 g of water were further added to the residual upper layer, which was separated again into a n-hexane layer and an aqueous layer by the same procedures as described above to separate and remove the aqueous layer (hereinafter referred to as the lower layer (2), 382 g). The thus obtained n-hexane layer (1296 g) contained as the result of analysis by the ethyl ether extraction method, 0.841 mol (365.8 g) of mono-2-decylpentadecyl phosphate, 0.036 mol (27.8 g) of di-2-decylpentadecyl phosphate and 0.0008 mol (0.78 g) of orthophosphoric acid (99% recovery rate for phosphoric ester, 99% removal rate for orthophosphoric acid).

Further, the thus recovered 867 g of the phosphoric acid (lower layer (1)+lower layer (2)) contained 0.96 mol (94.1 g) of orthophosphoric acid, to which 75% orthophosphoric acid at the food additive grade was supplemented, as required and which was concentrated to 100 to 101% concentration converted as orthophosphoric acid in the same manner as described above. Then, phosphorus pentaoxide was added in the same quantity ratio as described above and mixed sufficiently to obtain 116% polyphosphoric cid.

EXAMPLE 4

A mixture comprising 250 parts by weight of monolauryl phosphate and 400 parts by weight of orthophosphoric acid was placed in an extraction vessel. After heating to 50° C., 370 parts by weight of n-hexane, 70 parts by weight of isopropanol and 190 parts by weight of water were added and stirred at 50° C. for 30 minutes. Then, after interrupting the stirring, and allowing to stand still at 50° C. for 30 minutes to separate the layers, the lower layer was removed. 190 parts by weight of water and 70 parts by weight of isopropanol were added to the residual upper layer, which was separated into an upper layer and a lower layer by the same procedures as described above. As the result of the analysis for the upper and the lower layers, the removal rate was 95% for orthophosphoric acid and the recovery rate for monolauryl phosphate was more than 99%.

EXAMPLE 5

A mixture comprising 990 parts by weight of monocetyl phosphate and 620 parts by weight of orthophosphoric acid was placed in an extraction vessel. Then, after adding 2270 parts by weight of n-hexane, 560 parts by weight of isopropanol and 750 parts by weight of water and stirring at 50° C. for 30 minutes, they were left still at 50° C. for 30 minutes. After confirming the separation into upper and lower layers, the lower layer was removed. 150 parts by weight of isopropanol and 750 parts by weight of water were added again to the residual upper layer, which was separated into an upper layer and a lower layer in the same procedures as described above. As the result of the analysis, the recovery rate for monocetyl phosphate and 98% and the removal rate for orthophosphoric acid was 97%.

EXAMPLE 6

A mixture comprising 420 parts by weight of mono2-hexyldecyl phosphate and 270 parts by weight of orthophosphoric acid was placed in an extraction vessel. Then, after adding 360 parts by weight of n-hexane, 190 parts by weight of ethanol and 320 parts by weight of water and stirring at 50° C. for 30 minutes, they were left still for 30 minutes. After the separation of upper and lower layers, the lower layer was removed. 330 parts by weight of water and 190 parts by weight of ethanol were added again to the residual upper layer which was stirred at 50° C. for 30 minutes and was left still for 30 minutes to separate into an upper layer and a lower layer by the same procedures. As the result of analysis, the removal rate was 97% for orthophosphoric acid and the recovery rate for mono-2-hexyldecyl phosphate was 93%.

EXAMPLE 7

A mixture comprising 490 parts by weight of mono-2-undecylhexadecyl phosphate, 200 parts by weight of orthophosphoric acid and 50 parts by weight of di-2-undecylhexadecyl phosphate was placed in an extraction vessel. Then after adding 320 parts by weight of n-hexane, 410 parts by weight of water and 190 parts by weight of ethanol and stirring at 50° C. for 30 minutes, they were left still while being kept at 50° C. After confirming the separation into upper and lower layers, the lower layer was removed. 190 parts by weight of ethanol and 410 parts by weight of water were added to the residual upper layer, which was stirred at 50° C. for 30 minutes and then left still at 50° C. After confirming the separation of layers, the upper layer is isolated. As the result of analysis, the removal rate was 97% for orthophosphoric acid and the recovery rate for mono-2-undecylhexadecyl phosphate was 94%.

EXAMPLE 8

A mixture comprising 700 parts by weight of monolauryl phosphate, 250 parts by weight of dilauryl phosphate and 4 parts by weight of orthophosphoric acid was placed in an extraction vessel. 950 parts by weight of petroleum ether, 200 parts by weight of wate and 100 parts by weight of ethanol were added and stirred at room temperature for more than 30 minutes, left still and separated into upper and lower layers. As the result of the analysis, the removal rate was 98% for orthophosphoric acid and the recovery rate for mono- and dilauryl phosphate was 95%.

EXAMPLE 9

Figure 1:
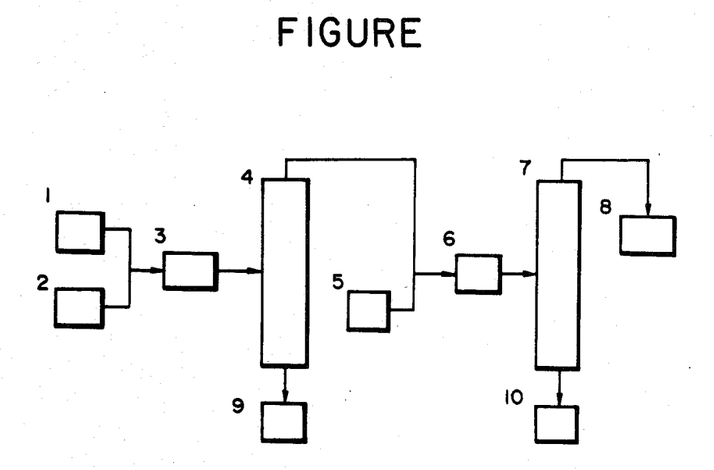
The sole figure is an explanatory diagram for the step showing the embodiment of practicing the second invention of the present application.

This invention was practiced as described below in accordance with the illustrative step diagram shown in the sole FIGURE.

(1) 380 parts by weight of n-hexane added to a mixture comprising 300 parts by weight of monolauryl phosphate and 470 parts by weight of orthophosphoric acid, and (2) 32% by weight of an aqueous isopropanol solution were fed at 174 g/hr and 425 g/hr into a mixing vessel (3) where it was continuously mixed and supplied to a separation vessel (4).

The upper layer (lighter fluid) flowing out from the upper portion of the vessel (4) was further mixed continuously with 27% by weight of an aqueous isopropanol solution (5) flowing at 23 g/hr in a mixng vessel (6) and then supplied to a separation vessel (7). There were obtained a lighter liquid removed with orthophosphoric acid from the upper portion of the vessel (7) and lower layer (heavier liquid) containing the removed orthophosphoric acid from the lower portion of the vessels (4), (7). The entire step was operated at 50° C.

As the result of analysis, the removal rate for orthophosphoric acid was 95% and the recovery rate for monolauryl phosphate was 99%.

COMPARATIVE EXAMPLE 1

180 parts by weight of hexane and 90 parts by weight of water were added to a mixture comprising 130 parts by weight of monolauryl phosphate and 190 parts by weight of orthophosphoric acid after being stirred for 30 minutes. Then after standing still, they were separated into an upper layer and a lower layer. As the result of analysis, the removal rate for orthophosphoric acid was 64% and the recovery rate for monolauryl phosphate was 87%.

EXAMPLE 10

A mixture comprising 250 parts by weight of monododecyl phosphate, 7 parts by weight of didodecyl phosphate and 400 parts by weight of orthophosphoric acid was placed in an extraction vessel, to which 370 parts by weight of n-hexane, 70 parts by weight of isopropanol and 190 parts by weight of water were added and stirred at 50° C. for 30 minutes. Then, after interrupting the stirring, and allowing to stand still at 50° C. for 30 minutes, the separated lower layer was extracted and removed. 190 parts by weight of water and 70 parts by weight of isopropanol were added to the residual upper layer and, after stirring at 50° C. for 30 minutes again, they were allowed to stand still for 30 minutes and the separated lower layer was withdrawn to obtain 828 parts by weight of an upper (n-hexane layer) containing monododecyl phosphate and removed with orthophosphoric acid. As the result of analysis, it contained 247 parts by weight (30%) of monododecyl phosphate, 6.5 parts by weight (.8%) of didodecyl phosphate, 17 parts by weight (2%) of orthophosphoric acid, 102 parts by weight (12%) of isopropanol and 85 parts by weight (10%) of water (recovery rate for monododecyl phosphate was 99% and removal rate for orthophosphoric acid was 96%).

The isopropanol was determined by gas chromatography for the sample and water was determined by Karl Fisher method. The analytical methods used in this example were also applied to the analysis for isopropanol and water in the subsequent Examples and Comparative Examples.

3020 parts by weight of n-hexane were continuously added to the residual upper layer, and water and isopropanol were azeotropically distilled off under heating together with n-hexane to finally heat the mixture up to 70° C. Analysis conducted at this stage for isopropanol and water showed that none of isopropanol and water was contained and they could be removed.

180 parts by weight of n-hexane were added to the residual mixture (liquid content 67%), and the solution was cooled at 5° C. Deposited crystals were collected through filtration and dried under a reduced pressure of 20 mmHg at 30° C. for 5 hours. 242 parts by weight of crystals were obtained, which were analyzed to show that 235 parts by weight of monododecyl phosphate and 7 parts by weight of orthophosphoric acid were contained. Further, water and isopropanol were not contained and there was no problem such as odors of isopropanol.

The analytical values at each of the stages were summarized as below:

| | |
|---|---|
| 1. Recovery rate of monododecyl phosphate from the separated upper layer | 99% |
| 2. Removal rate for orthophosphoric acid | 96% |
| 3. Content of monododecyl phosphate in the upper layer after the extracting separation | 30% |
| 4. Content of phosphoric acid in the upper layer after the extracting separation | 2% |
| 5. Content of isopropanol in the upper layer after the extracting separation | 12% |
| 6. Content of water in the upper layer after the extracting separation | 10% |
| 7. Content of water after azeotropic removal | 0% |
| 8. Content of isopropanol after azeotropic | 0% |

| | |
|---|---|
| *-continued* | |
| removal | |
| 9. Content of monododecyl phosphate after purification | 97.1% |
| 10. Content of didodecyl phosphate after purification | 0% |
| 11. Content of orthophosphoric acid after purification | 2.9% |
| 12. Content of isopropanol after purification | 0% |
| 13. Content of water after purification | 0% |

EXAMPLE 11

A mixture comprising 990 parts by weight of monohexadecyl phosphate, and 620 parts by weight of orthophosphoric acid was placed in an extraction vessel, to which 2270 parts by weight of n-hexane, 560 parts by weight of isopropanol and 750 parts by weight of water were added, stirred at 50° C. for 30 minutes and then left still at 50° C. for 30 minutes.

After confirming the separation into upper and lower layers, the lower layer was withdrawn from the vessel.

150 parts by weight of isopropanol and 750 parts by weight of water were added again to the residual layer and, after stirring at 50° C. for 30 minutes again, they were allowed to stand still for 30 minutes and the lower layer was withdrawn again to obtain 3970 parts by weight of an upper layer (n-hexane layer) containing monohexadecyl phosphate and removed with orthophosphoric acid.

3400 parts by weight of n-hexane were continuously added to the residual upper layer to azeotropically distill off water and isopropanol under heating together with n-hexane to finally heat up to 80° C. Analysis conducted at this stage for isopropanol and water showed that none of isopropanol and water was contained. Further, they were dried under a reduced pressure (20 mmHg) at 50° C. for 5 hours for completely removing n-hexane to obtain 989 parts by weight of white powder. The powder was analyzed to contain 970 parts by weight of monohexadecyl phosphate and 18.6 parts by weight of orthophosphoric acid. Further, water and isopropanol were not contained and there was no problem such as odors of isopropanol.

The analytical values at each of the stages are summarized as below:

| | |
|---|---|
| 1. Recovery rate of monohexadecyl phosphate from the separated upper layer | 98% |
| 2. Removal rate for orthophosphoric acid | 97% |
| 3. Content of monohexadecyl phosphate in the upper layer after the extracting separation | 24.4% |
| 4. Content of phosphoric acid in the upper layer after the extracting separation | 0.5% |
| 5. Content of isopropanol in the upper layer after the extracting separation | 10% |
| 6. Content of water in the upper layer after the extracting separation | 8% |
| 7. Content of water after azeotropic removal | 0% |
| 8. Content of isopropanol after azeotropic removal | 0% |
| 9. Content of monohexadecyl phosphate after purification | 98% |
| 10. Content of orthophosphoric acid after purification | 1.9% |
| 11. Content of isopropanol after purification | 0% |
| 12. Content of water after purification | 0% |

EXAMPLE 12

A mixture comprising 490 parts by weight of mono-2-undecylhexadecyl phosphate, 200 parts by weight of orthophosphoric acid and 30 parts by weight of di-2-undecylhexadecyl phosphate was placed in an extraction vessel, to which 820 parts by weight of n-hexane, 410 parts by weight of water and 190 parts by weight of ethanol were added and stirred at 50° C. for 30 minutes while keeping the temperature. Then, they were left still while being kept at 50° C. After confirming the separation into upper and lower layers, the lower layer was withdrawn.

190 parts by weight of ethanol and 410 parts by weight of water were added again to the residual upper layer and the mixture was stirred at 50° C. for 30 minutes again. Further, they were left still at 50° C. and after confirming the separation into upper and lower layers, the lower layer was withdrawn to obtain 1682 parts by weight of an upper layer (n-hexane layer) containing mono-2-undecylhexadecyl phosphate and being removed with orthophosphoric acid.

To the residual n-hexane solution containing the phosphoric ester, were further added dropwise 3520 parts by weight of n-hexane continuously. Then they were heated to remove residual water and ethanol through azeotropic distillation together with n-hexane and the residue was finally heated up to 80° C. When analyzed at this stage for isopropanol and water, none of them was contained. Further, the residue was dried under a reduced pressure (20 mmHg) at 50° C. for 5 hours for completely removing n-hexane to obtain 534 parts by weight of white powder. As the result of analysis, the powder contained 475 parts by weight of mono-2-undecylhexadecyl phosphate, 47 parts by weight of di-2-undecylhexadecyl phosphate and 12 parts by weight of orthophosphoric acid. Water and isopropanol were not contained.

The analytical values at each of the stages are summarized below:

| | |
|---|---|
| 1. Recovery rate of mono-2-undecylhexadecyl phosphate from the separated upper layer | 97% |
| 2. Removal rate for orthophosphoric acid | 94% |
| 3. Content of mono-2-undecylhexadecyl phosphate in the upper layer after the extracting separation | 28.2% |
| 4. Content of phosphoric acid in the upper layer after the extracting separation | 0.7% |
| 5. Content of ethanol in the upper layer after the extracting separation | 9.7% |
| 6. Content of water in the upper layer after the extracting separation | 9.8% |
| 7. Content of water after azeotropic removal | 0% |
| 8. Content of isopropanol after azeotropic removal | 0% |
| 9. Content of mono-2-undecyldexadecyl phosphate after purification | 89% |
| 10. Content of di-2-undecylhexadecyl phosphate after purification | 8.8% |
| 11. Content of orthophosphoric acid after purification | 2.2% |
| 12. Content of ethanol after purification | 0% |
| 13. Content of water after purification | 0% |

COMPARATIVE EXAMPLE 2

A mixture comprising 250 parts by weight of monododecyl phosphate, 7 parts by weight of didodecyl phosphate and 400 parts by weight of orthophosphoric acid was placed in an extraction vessel in the same manner as in Example 10, to which n-hexane, water and isopropanol each in the same amount as in Example 1 were added and subjected to the similar procedures (twice extracted) to obtain 824 parts by weight of an upper layer (n-hexane layer) containing monododecyl phosphate. As the result of the analysis, 245 parts by weight of monododecyl phosphate, 6 parts by weight of didodecyl phosphate, 16 parts by weight of orthophosphoric acid, 100 parts by weight of isopropanol and 87 parts by weight of water were contained.

The liquid mixture was cooled to −5° C. to crystallize the monododecyl phosphate, followed by filtration. The crystals obtained were viscous and did not show definite crystal form, while the crystals in Example 10 were fine plate-like form. Further, when the crystals were dried in the same manner as in Example 10, 157 parts by weight of the white powder were obtained. As the result of analysis of the powder, 135 parts by weight of monododecyl phosphate, 4 parts by weight of didodecyl phosphate, 12 parts by weight of orthophosphoric acid, 1 part by weight of isopropanol and 5 parts by weight of water were contained. Odors of isopropanol could not be eliminated.

The recovery rate for monododecyl phosphate upon recrystallization was 55% as compared with 95% in the case of Example 10.

COMPARATIVE EXAMPLE 3

A mixture comprising 990 parts by weight of monohexadecyl phosphate and 620 parts by weight of orthophosphoric acid was placed in an extraction vessel in the same manner as in Example 11 and subjected to the same procedures (twice extracted) as in Example 11 to obtain 3974 parts by weight of a n-hexane layer containing monohexadecyl phosphate. As the result of analysis of the resultant product, 975 parts by weight of monohexadecyl phosphate, 17.5 parts by weight of orthophosphoric acid, 385 parts by weight of isopropanol and 326 parts by weight of water were obtained.

The product was further subjected as it was to topping under heating without adding n-hexane, dried under a reduced pressure for distilling off the solvent in the same manner as in Example 11 to obtain 1018 parts by weight of white powder. As the result of analysis of the powder, 975 parts by weight of monohexadecyl phosphate, 17.5 parts by weight of orthophosphoric acid, 5 parts by weight of isopropanol and 20 parts by weight of water were contained. The odor of isopropanol could not be eliminated.

COMPARATIVE EXAMPLE 4

180 parts by weight of n-hexane and 90 parts by weight of water were added to a mixture comprising 130 parts by weight of monododecyl phosphate and 190 parts by weight of orthophosphoric acid and were stirred for 30 minutes. Then, after allowing to stand still and confirming the separation of layers, they were separated into an upper layer and a lower layer.

As the result of analysis of the upper layer, 113 parts by weight of monododecyl phosphate and 68.5 parts by weight of orthophosphoric acid were contained (removal rate for orthophosphoric acid: 64%, recovery rate for mono-dodecyl phosphate: 87%).

What is claimed is:

1. A process for purifying a monoalkyl phosphoric ester having 8-32 C atoms from a mixture comprising said monoalkyl phosphoric ester and orthophosphoric acid, which comprises:

adding, as a solvent, (a) one or more materials selected from the group consisting of linear or branched saturated aliphatic hydrocarbons having from 4 to 8 carbon atoms and saturated cycloaliphatic hydrocarbons having from 5 to 7 carbon atoms and (b) a lower alcohol having from 1 to 4 carbon atoms and water to said mixture thereby isolating and separating the phosphoric ester in the hydrocarbon phase.

2. The purification process as defined in claim 1, wherein the phosphoric ester mainly consists of a compound represented by the following general formula (I):

where R represents a linear or branched alkyl or alkenyl group having from 8 to 36 carbon atoms.

3. The purification process as defined in claim 1, wherein the lower alcohol is isopropanol.

4. A process for purifying a phosphoric ester, which comprises adding to a mixture containing a phosphoric ester and orthophosphoric acid, (a) at least one material selected from the group consisting of linear or branched saturated aliphatic hydrocarbons having from 4 to 8 carbon atoms and saturated cycloaliphatic hydrocarbons having from 5 to 7 carbon atoms and (b) a lower alcohol having from 1 to 4 carbon atoms and water, isolating the phosphoric ester into the hydrocarbon phase, removing the lower alcohol and water incorporated into the hydrocarbon phase through azeotropic distillation to produce a residue and then recrystallizing or topping the residue.

5. The process of claim 1, wherein said phosphoric ester is monooctyl phosphate, monodecyl phosphate, monooctadecyl phosphate, monotetracosyl phosphate, monooctacosyl phosphate, monooctenyl phosphate, monooctadecenyl phosphate, monotetracosenyl phosphate, mon-2-hexyldecyl phosphate, mono-2-octylundecyl phosphate or mono-2-tetradecyloctadecyl phosphate.

6. The process of claim 4, wherein said phosphoric ester is monooctyl phosphate, monodecyl phosphate, monooctadecyl phosphate, monotetracosyl phosphate, monooctacosyl phosphate, monooctenyl phosphate, monooctadecenyl phosphate, monotetracosenyl phosphate, mono-2-hexyldecyl phosphate, mono-2-octylundecyl phosphate or mono-2-tetradecyloctadecyl phosphate.

* * * * *